(12) United States Patent
Carasso et al.

(10) Patent No.: US 8,417,316 B2
(45) Date of Patent: Apr. 9, 2013

(54) MRI IMAGING AND CONTRAST METHOD

(75) Inventors: Dina Carasso, Kfar-Saba (IL); Uzi Eliav, Tel-Aviv (IL); Gil Navon, Ramat-Gan (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 11/661,975

(22) PCT Filed: Sep. 8, 2005

(86) PCT No.: PCT/IL2005/000958
§ 371 (c)(1),
(2), (4) Date: Mar. 6, 2007

(87) PCT Pub. No.: WO2006/027783
PCT Pub. Date: Mar. 16, 2006

(65) Prior Publication Data
US 2008/0091099 A1    Apr. 17, 2008

Related U.S. Application Data

(60) Provisional application No. 60/607,589, filed on Sep. 8, 2004.

(51) Int. Cl.
*A61B 5/055* (2006.01)

(52) U.S. Cl.
USPC .......... 600/410; 600/407; 600/409; 600/411; 600/412; 324/300

(58) Field of Classification Search ................ 600/407, 600/409–412; 324/300, 309, 310
See application file for complete search history.

(56) References Cited

U.S. PATENT DOCUMENTS

| 6,263,228 | B1 | 7/2001 | Zhang | |
|---|---|---|---|---|
| 6,589,174 | B1 * | 7/2003 | Chopra et al. | 600/439 |
| 2004/0010191 | A1 | 1/2004 | Yatsui | |

FOREIGN PATENT DOCUMENTS

WO    WO 2006/027783    3/2006

OTHER PUBLICATIONS

Renou, J. P., et al., in NMR study of collagen-water interactions. Biopolymers, 1994. 34(12): p. 1615-26.*
International Preliminary Report on Patentability Dated Mar. 22, 2007 From the International Bureau of WIPO Re.: Application No. PCT/IL2005/000958.

* cited by examiner

*Primary Examiner* — Tse Chen
*Assistant Examiner* — Vani Gupta

(57) ABSTRACT

A novel MRI contrast technique enables to observe tissue properties not observable by previously known MRI methods. A difference between two disclosed pulse sequences is used to measure magnetization exchange time between water molecules and macromolecules such as proteins, thereby producing a measure highly sensitive to tissue changes resulting from coagulation, yet relatively insensitive to temperature fluctuations. This result is applied to an imaging method and provides direct visualization of the effects of surgical thermal ablation procedures.

24 Claims, 3 Drawing Sheets

MRI IMAGING AND CONTRAST METHOD

RELATED APPLICATIONS

This Application is a National Phase of PCT Patent Application No. PCT/IL2005/000958 having International Filing Date of Sep. 8, 2005, which claims the benefit of U.S. Provisional Patent Application No. 60/607,589 filed on Sep. 8, 2004. The contents of the above Applications are all incorporated herein by reference.

FIELD AND BACKGROUND OF THE INVENTION

The present invention relates to a novel MRI contrast approach for imaging of tissue and in particular ablated tissue.

Various MRI techniques are used to obtain contrast between different tissues as well as between normal and pathological states of same tissues. Examples are: T1 and T2 weighted, proton density, diffusion weighted and MTC, each being used for different imaging and diagnostic purposes.

Utilizing imaging modalities to evaluate damage done to a surgical ablation target and to tissues near a surgical ablation target is an essential aspect of many surgical techniques. Tissue damage evaluation is typically done both during surgical use of thermal ablation procedures and subsequent to such use. Yet accurate evaluation of tissue damage is difficult to achieve. None of the MRI techniques listed above enables direct visualization of tissue damage, nor enables to distinguish between coagulated and non-coagulated tissues.

Thermal ablation techniques include heating techniques such as heating with RF energy, with microwave energy, with focused ultrasound, and with laser light, and cooling techniques such as evaporative cryoablation and Joule-Thomson cryoablation. Monitoring of the effects of application of these techniques is typically accomplished indirectly, by measuring tissue temperatures. Yet even in the case of those thermal therapy techniques which enable incorporation of use of thermometers and thermocouples during procedures, temperature is measured only at discrete points, such as at the operating tips of thermometers, and therefore does not provide an accurate indication of temperature throughout the affected tissue. Consequently, MRI is a preferred method for measuring tissue temperatures.

The most commonly used MRI methods for measuring temperature are the T1-weighted method and the proton resonance frequency (PRF) method.

The T1-weighted method is discussed by Dick, E. A., et al., MR-guided laser thermal ablation of primary and secondary liver tumours. Clin Radiol, 2003. 58(2): p. 112-20, by Fiedler, V. U., et al., Laser-induced interstitial thermotherapy of liver metastases in an interventional 0.5 Tesla MRI system: technique and first clinical experiences. J Magn Reson Imaging, 2001. 13(5): p. 729-37, by Morrison, P. R., et al., MRI of laser-induced interstitial thermal injury in an in vivo animal liver model with histologic correlation. J Magn Reson Imaging, 1998. 8(1): p. 57-63, and by Matsumoto, R., et al., Tissue temperature monitoring for thermal interventional therapy: comparison of T1-weighted MR sequences. J Magn Reson Imaging, 1994. 4(1): p. 65-70.

Proton resonance frequency (PRF) methods are discussed by Palussiere, J., et al., Feasibility of MR-guided focused ultrasound with real-time temperature mapping and continuous sonication for ablation of VX2 carcinoma in rabbit thigh. Magn Reson Med, 2003. 49(1): p. 89-98, and by Weidensteiner, C., et al., Real-time NM temperature mapping of rabbit liver in vivo during thermal ablation. Magn Reson Med, 2003. 50(2): p. 322-30.

MRI methods for temperature measurement suffer from a variety of drawbacks and limitations. These include the following:

(1) Spin-echo sequences cannot be used for PRF methods since the temperature-induced phase contribution will be refocused. Optimal TE for PRF is equal to T2*, as discussed by de Zwart, J. A., et al., Fast magnetic-resonance temperature imaging. J Magn Reson B, 1996. 112(1): p. 86-90. For tissues with short T2*(such as the liver) the method is difficult to perform and the signal-to-noise ratio is small, as discussed in Weidensteiner, C., et al., Stability of real-time MR temperature mapping in healthy and diseased human liver. J Magn Reson Imaging, 2004. 19(4): p. 438-46.

(2) Temperature-dependent changes in magnetic susceptibility and conductivity contribute to errors in PRF. These factors are discussed in Peters, R. D., R. S. Hinks, and R. M. Henkelman, Heat-source orientation and geometry dependence in proton-resonance frequency shift magnetic resonance thermometry. Magn Reson Med, 1999. 41(5): p. 909-18, Peters, R. D. and R. M. Henkelman, Proton-resonance frequency shift MR thermometry is affected by changes in the electrical conductivity of tissue. Magn Reson Med, 2000. 43(1): p. 62-71, and in De Poorter, J., Noninvasive MRI thermometry with the proton resonance frequency method: study of susceptibility effects. Magn Reson Med, 1995. 34(3): p. 359-67.

(3) The PRF method suffers from motion artifacts, as discussed in Fiedler op. cit. PRF is based on the phase difference between two complex gradient-echo MR images, and thus is sensitive to motion artifacts in mobilized organs and tissues, such as the liver. See also Rieke, V., et al., Referenceless PRF shift thermometry. Magn Reson Med, 2004. 51(6): p. 1223-31.

(4) PRF thermometry can be applied usefully only in mid or high field ($\geq 1$ T). See Germain, D., et al., MR monitoring of tumour thermal therapy. Magma, 2001. 13(1): p. 47-59, and Quesson, B., J. A. de Zwart, and C. T. Moonen, Magnetic resonance temperature imaging for guidance of thermotherapy. J Magn Reson Imaging, 2000. 12(4): p. 525-33.

(5) T1 is sensitive to coagulation also, therefore giving inaccurate estimation of temperature as necrosis develops, when using T1 weighted sequences. This problem is discussed in Graham, S. J., M. J. Bronskill, and R. M. Henkelman, Time and temperature dependence of MR parameters during thermal coagulation of ex vivo rabbit muscle. Magn Reson Med, 1998. 39(2): p. 198-203.

In addition to the above-noted limitations in accuracy and practicality of MRI temperature measurement, it may further be noted that once temperatures have been measured using T1-weighted or proton resonance frequency techniques, the extent of damage to examined tissue can only be roughly inferred or estimated by calculation based on the temperature. Tissue damage estimations based on such calculations are thus intrinsically indirect and necessarily somewhat inaccurate. These calculation methods are discussed in Graham, S. J., et al., Quantifying tissue damage due to focused ultrasound heating observed by MRI, Magn Reson Med, 1999. 41(2): p. 321-8, and Ishihara, Y., et al., A precise and fast temperature mapping using water proton chemical shift, Magn Reson Med, 1995. 34(6): p. 814-23.

In sum, estimation of damage to tissue on the basis of the temperature measurement suffers from inherent inaccuracies, and is susceptible to variations from one patient to another.

Thus, there is a widely recognized need for, and it would be highly advantageous to have, a method of directly measuring physical changes brought about in ablated tissue by thermal ablation.

It is further noted that currently popular methods for evaluating results of thermal therapies use T2-weighted and gadolinium contrast enhanced T1-weighted MR lesion images as a predictor of eventual cell death. This technique is discussed in Breen M S, Lazebnik R S, Fitzmaurice M, Nour S G, Lewin J S, Wilson D L. *Radiofrequency thermal ablation: correlation of hyperacute MR lesion images with tissue response*. J Magn Reson Imaging 2004; 20(3):475-486. For clinical treatments of patients with liver tumors, Vogl. et al. used contrast enhanced FLASH 2d sequences to give information about size of the coagulated tissue. This process also includes the injection of contrast agent, as discussed in Vogl T J, Mack M G, Muller P K, Straub R, Engelmann K, Eichler K. *Interventional MR: interstitial therapy*. Eur Radiol 1999; 9(8):1479-1487. Wacker et al. used gadolinium enhanced T1 weighted imaging for the follow stage, as discussed in Wacker F K, Reither K, Ritz J P, Roggan A, Germer C T, Wolf K J. *MR-guided interstitial laser-induced thermotherapy of hepatic metastasis combined with arterial blood flow reduction: technique and first clinical results in an open MR system*. J Magn Reson Imaging 2001; 13(1):31-36.

However, injections of gadolinium and similar contrast agents are invasive procedures and are therefore generally disadvantageous and may in some cases be specifically contra-indicated because of existing clinical conditions. Thus, there is a widely recognized need for, and it would be highly advantageous to have, a method of directly measuring physical changes brought about in ablated tissue by thermal ablation without necessitating injection of contrast agents into the body.

SUMMARY OF THE INVENTION

According to one aspect of the present invention there is provided a method of imaging a tissue comprising exposing the tissue to MR pulses which result in a proton magnetization exchange between water molecules and macromolecules of the tissue, and processing a water signal resulting from the proton magnetization exchange between the water molecules and the macromolecules, thereby imaging the tissue. The method optionally further comprises use of a magnetic image generation technique operable to display physical properties of a tissue.

According to further features in preferred embodiments of the invention described below, the processing of the water signal comprises calculating a difference between a first water signal influenced by the magnetization exchange and a second water signal substantially uninfluenced by the magnetization exchange.

According to still further features in preferred embodiments of the invention described below, the method comprises calculating a difference between a first signal generated in response to a first pulse sequence of the MR pulses and a second signal generated in response to a second pulse sequence of the MR pulses, the first and second pulse sequences having in common a first pulse, a second pulse, and third pulse, wherein a first time interval between the first and the second pulses of the first signal is sufficiently long to allow relaxation of transverse magnetization of the macromolecules and sufficiently short to prevent significant relaxation of transverse magnetization of the water molecules; and a second time interval between the second pulse and the third pulse of the first signal is sufficiently long to allow substantial transfer of magnetization from the water molecules to the macromolecules.

According to yet further features in preferred embodiments of the invention described below, a third time interval between the first and the second pulses of the second pulse sequence is sufficiently short to prevent substantial relaxation of transverse magnetization of the macromolecules during the third interval. Alternatively, a fourth time interval between the second pulse and the third pulse of the second pulse sequence is sufficiently short to prevent substantial transfer of magnetization from the water molecules to the macromolecules.

The third pulses of the first and second pulse sequences may be 90° pulses, and may be selective pulses coordinated with use of a standard MRI imaging technique. In a preferred embodiment the third pulse of at least the first pulse sequence is a selective pulse followed by a fast spin echo or by a gradient echo.

The first pulses of the first and second pulse sequences may be 90° pulses, and the second pulses of the first and second pulse sequences may be 90° pulses.

According to further features in preferred embodiments of the invention described below, it is possible to select a timing delay for the second interval such that a signal is detected from coagulated tissue, and also possible to select a timing delay for the second interval such that no signal is detected from coagulated tissue.

Preferred embodiments include those in which the first time interval between the first and the second pulses of the first pulse sequence is different from a third time interval between the first and the second pulses of the second pulse sequence, and those in which the second time interval between the second pulse and the third pulse of the first pulse sequence is different from a fourth time interval between the second pulse and the third pulse of the second pulse sequence.

The third pulses of the first and second MR pulse sequences may be soft pulses used for slice selection as part of an MR imaging technique. Similarly, the first pulses and second pulses of the first and second MR pulse sequences may be soft pulses suitable for use in a clinical scanner, or all the MR pulses used may be soft pulses. According to another aspect of the present invention there is provided a method for measuring the effect of thermal treatments of a tissue, comprising exposing the tissue to MR pulses which result in a magnetization exchange between water molecules and macromolecules of the tissue, and processing a water signal resulting from the magnetization exchange between the water molecules and the macromolecules, thereby imaging the tissue. Such imaging may be used subsequent to thermal treatment of the tissue, or during thermal treatment of tissue, to reveal tissue regions exhibiting coagulation. Similarly, the method may be used to monitor other changes in properties of tissues both during and after thermal treatment. In a preferred embodiment, the tissue so imaged is liver tissue.

The present invention successfully addresses the shortcomings of the presently known configurations by providing a novel MRI contrast technique enabling to observe tissue properties not observable by previously suggested MRI methods.

The present invention further successfully addresses the shortcomings of the presently known configurations by providing a method for directly measuring physical changes brought about in ablated tissue by thermal ablation, which methods successfully distinguish between ablated and not-ablated tissue, and are relatively unaffected by variations in temperature of the examined tissues.

The present invention further successfully addresses the shortcomings of the presently known configurations by providing a method for measuring the influence of thermal therapies on tissue, which method does not require injection of a contrast medium into the patient.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
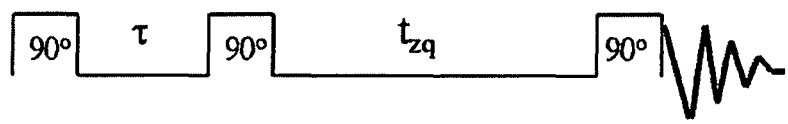
FIG. 1 presents an MR pulse sequence useable to measure the proton magnetization exchange time $\tau_{MEX}$ between water and macromolecules such as proteins in body tissue, according to an embodiment of the present invention.

The present invention is of a novel MRI contrast technique enabling to observe tissue properties not observable by previously known MRI methods. Specifically, a disclosed pulse sequence and signal processing procedure is used to measure magnetization exchange time between water and macromolecules such as proteins, which measure is used to distinguish between coagulated and non-coagulated tissues, thereby providing means and method for direct monitoring of thermal ablation of tissues of a body.

The suggested technique is extremely appropriate to monitor ablation procedures, as it is highly sensitive to changes in the tissue resulting from coagulation of the tissue. The technique is also expected to be useful for diagnosing and localizing a variety of other pathological conditions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Various MRI imaging approaches are known in the art. Although such approaches can be used to image various tissue types, they are limited in that they do not provide a method for contrasting coagulated to non-coagulated tissue. Existing popular methods allowing to deduce or predict the presence of coagulated tissue require injection of a potentially toxic contrast medium into the patient.

While reducing the present invention to practice, the present inventors have uncovered an MRI contrast method which enables direct visualization of tissue properties which cannot be directly visualized by prior art methods. The methods presented herein are based on the inventor's observation that body tissues vary with respect to the speed with which magnetization is exchanged between protons of water molecules and protons of macromolecules of the tissue. Consequently, measurement of proton magnetization exchange time (herein "$\tau_{MEX}$") provides means for discriminating between tissues of various sorts. In a particularly useful embodiment, measurement of magnetization exchange time enables to distinguish between coagulated and non-coagulated tissue, since magnetization exchange has been observed to be significantly faster in coagulated tissue than in non-coagulated tissue. Consequently it is possible to select and use an MR pulse sequence having an interval for magnetization exchange such that significant exchange can be detected in coagulated tissue, while significantly less magnetization exchange is detected from non-coagulated tissue. Combining such a pulse sequence with a standard MRI imaging sequence enables to selectively image coagulated or non-coagulated tissue at will.

Thus, according to one aspect of the present invention there is provided a method of imaging a tissue. The method is effected by exposing the tissue to magnetic resonance (MR) pulses which provoke a proton magnetization exchange between water and macromolecules of the tissue, and processing a water signal resulting from the proton magnetization exchange between the water and said macromolecules.

As used herein, the term macromolecules refers to any large organic molecule composed of multiple small structural units linked together. Proteins and nucleic acids are examples of macromolecules as that term is used herein.

Although any number and type of MR pulse sequences can be used with the present approach, the present invention preferably utilizes two pulse sequences, a first sequence resulting in proton magnetization exchange between water molecules and macromolecules, and a second sequence designed to avoid such proton magnetization exchange. When a first signal resulting from use of the first pulse sequence and a second signal resulting from use of the second pulse sequence are subtracted one from the other, the result is a difference signal strongly influenced by the magnetization exchange. This resultant difference signal may then be used to characterize and to image the tissue.

The method can be applied in any clinical MRI scanner, as it only requires the addition of two appropriately timed pulses before a user-selected standard imaging sequence.

Any tissue can be imaged with the suggested method. As is further described hereinbelow, the present approach is highly suitable for imaging ablated tissue and thus can be utilized during or following medical procedures which employ thermal tissue ablation techniques, yet the technique is also useful for various additional purposes of MR scanning. The method of the present invention provides superior contrast between coagulated and healthy tissue, but may also be useful for recognizing and localizing a variety of other tissue pathologies.

A more detailed description of the present method and of one specific use thereof is provided in FIGS. 1-4.

Attention is now drawn to FIG. 1, which presents an MR pulse sequence useable to measure the magnetization exchange time $\tau_{MEX}$ between water and macromolecules such as proteins in body tissue, according to an embodiment of the present invention. The MR pulse sequence presented in FIG. 1 bears similarity to that presented by Renou, J. P., et al., in their *Study of the water—collagen system by NMR cross relaxation experiments*. J Biochem Biophys Methods, 1983. 7(2): p. 91-9, and Renou, J. P., et al., in *NMR study of collagen-water interactions*. Biopolymers, 1994. 34(12): p. 1615-26. In those studies Renou et al. report measurement of cross relaxation by proton exchange and dipolar interaction between water and purified collagen.

Calculations based on responses to the pulse sequence presented in FIG. 1 may be used to isolate a signal exclusively or substantially dependent on magnetization exchange between water molecules and macromolecules such as proteins. In the pulse sequence presented in FIG. 1, the first 90° pulse transfers both the water and the macromolecule magnetization into the XY plane. The macromolecule transverse magnetization relaxes during τ on a very short time scale of a few tens of microseconds, while the water magnetization hardly decays. The second 90° pulse transfers the water magnetization back into the Z-axis. Then, during the time $t_{zq}$, water magnetization is transferred to the macromolecules, with proton magnetization exchange time $\tau_{MEX}$.

It is to be noted that the first and second pulses in the exemplary MR pulse sequence presented in FIG. 1 are 90° pulses. 90° pulses are indeed used in a presently preferred embodiment, but it is to be understood that the 90° angle here presented is exemplary only, and not to be considered limiting. Pulses with orientations other than 90° may be preferred, depending on the intended use of the data being analyzed and the material being examined. An example of use of pulse angles other than 90° will be presented hereinbelow.

$\tau_{MEX}$ can be measured and various tissue types or tissue conditions can be distinguished by varying the time $t_{zq}$. For example, since proton magnetization exchange is considerably faster in coagulated tissue than in non-coagulated tissue of the same type, time $t_{zq}$ may be set to an interval which results in generating a strong signal from coagulated tissue, and only a weak signal or no signal from non-coagulated tissue, as is demonstrated in the examples discussed hereinbelow.

In the signal received in response to the pulse sequence presented in FIG. 1, variation due to magnetization exchange is masked by the strong signal of water protons that do not exchange magnetization with the protein (or other macromolecule). The disclosed method therefore further comprises calculating a difference signal showing the difference between a first signal detected in response to the pulse sequence of FIG. 1, and a second signal representing that portion of the first signal which does not originate from the magnetization transfer to macromolecules. The resultant difference signal, strongly influenced by the magnetization transfer, may then be reported or used in an imaging sequence.

Two preferred embodiments comprising two different methods for creating the "second signal" (used in creating the difference signal) are proposed.

In a first embodiment (referred to as "method A" in the examples section hereinbelow), the second signal is obtained by utilizing a pulse sequence similar to that used to obtain the first signal, but with a very short $t_{zq}$, thereby generating a signal absent any magnetization exchange. This embodiment has been tested using soft pulses suitable for use in clinical scanners. Results similar to those obtained using hard pulses were observed.

In a second embodiment (referred to as "method B" in the examples section hereinbelow), the second signal is obtained using a pulse sequence similar to that used for the first signal, but having an interval τ shorter than the decay time of the protein magnetization. As a result, the macromolecule magnetization does not decay and decay as a result of exchange does not take place.

In both embodiments, subtraction of the second signal from the first signal produces a result which substantially corresponds to that portion of the first signal which results from and depends on magnetization exchange between water molecules and proteins or other macromolecules.

Thus, in a preferred embodiment, a method of imaging a tissue comprises exposing the tissue to MR pulses which result in a proton magnetization exchange between water molecules and macromolecules of the tissue, and processing a water signal resulting from said proton magnetization exchange between the water molecules and said macromolecules, thereby imaging the tissue. Processing of the water signal comprises calculating a difference between a first water signal influenced by the magnetization exchange and a second water signal substantially uninfluenced by the magnetization exchange.

The difference signal is calculated as a difference between a first signal generated in response to a first pulse sequence of MR pulses and a second signal generated in response to a second pulse sequence of said MR pulses. The first and second pulse sequences have in common a first pulse (a 90° pulse in our FIG. 1 example), a second pulse (also a 90° pulse in our FIG. 1 example), and third pulse. A first time interval between the first and second pulses of the first signal is sufficiently long to allow relaxation of transverse magnetization of the macromolecules and sufficiently short to prevent significant relaxation of transverse magnetization of the water molecules. A second time interval between the second pulse and the third pulse of the first signal is sufficiently long to allow substantial transfer of magnetization from the water molecules to the macromolecules.

In a first preferred embodiment, a third time interval between the first and second pulses of the second pulse sequence is sufficiently short to prevent substantial relaxation of transverse magnetization of the macromolecules during that third interval.

In an alternative preferred embodiment, a fourth time interval between the second pulse and the third pulse of the second pulse sequence is sufficiently short to prevent substantial transfer of magnetization from water molecules to macromolecules.

In both cases, the subtraction has the effect of eliminating the undesired signal of water protons that did not undergo magnetization exchange with macromolecules.

The proton magnetization exchange time ($\tau_{MEX}$), measured through the pulse sequence in FIG. 1 has only very weak sensitivity to temperature in the temperature range relevant to the thermal ablation process, but is very sensitive to coagulation. It is therefore a direct measure of ablated areas, and is not sensitive to temperature fluctuations. Consequently, measures of $\tau_{MEX}$ and imaging techniques based thereon may be utilized to provide operative and post-operative feedback for processes of thermal ablation.

For imaging purposes, the third pulses of the first and second pulse sequences may be selective pulses coordinated with use of one of a variety of standard MRI imaging techniques. For example, the third pulse may be a selective pulse followed by a fast spin echo, or by a gradient echo.

Figure 2A:
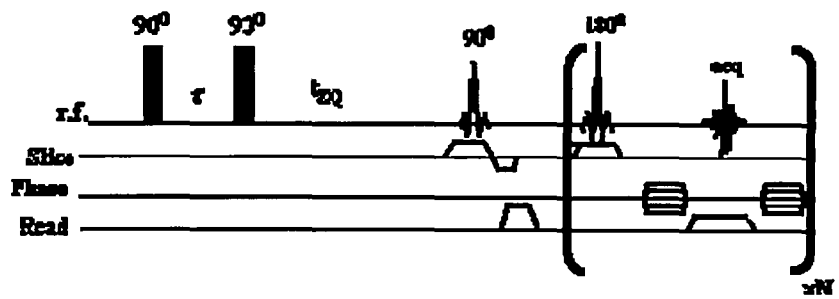
FIG. 2*a* presents a combination of the pulse sequence presented in FIG. 1 with spin echo imaging, according to an embodiment of the present invention.

Attention is now drawn to FIG. 2a which presents a combinations of combination of the pulse sequence presented in FIG. 1 with spin echo imaging, according to an embodiment of the present invention. In a process referred to herein as Magnetization Exchange Imaging ("MEXI"), the pulse sequence presented in FIG. 1 and discussed hereinabove may be combined with any imaging method, such as gradient echo, spin echo, etc. In other words, before a standard imaging sequence such as gradient echo or spin echo, two pulses are applied together with two delay intervals ($\tau$ and $t_{eq}$), as discussed above. An illustration of the method combined with fast spin echo (RARE) is shown in FIG. 2a. A selective pulse replaces the third pulse in the spectroscopy pulse sequence, and is followed by a fast spin echo.

Figure 2B:
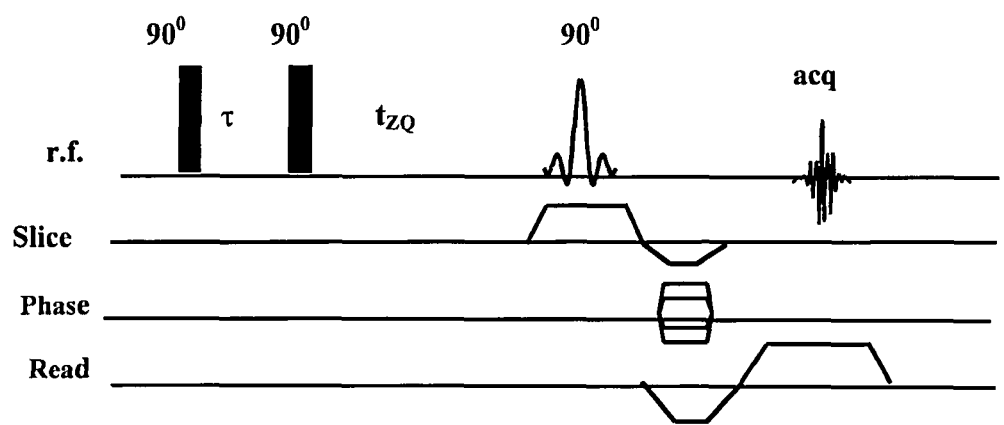
FIG. 2*b* presents a combination of the pulse sequence presented in FIG. 1 with gradient echo imaging, according to an embodiment of the present invention.

Attention is now drawn to FIG. 2b, which is combination of the pulse sequence presented in FIG. 1 with gradient echo imaging, according to an embodiment of the present invention. In similarity to the method presented in FIG. 2a, a selective pulse replaces the third pulse in the spectroscopy pulse sequence, and is followed by a gradient echo.

The selective pulses so used may be soft pulses, as used for slice selection in MR imaging techniques. The first and second pulses used in the pulse sequences described hereinabove may also be soft pulses suitable for use in a clinical scanner. Thus, in an alternative embodiment, all the MR pulses used in the method may be soft pulses.

The third pulses of the NM pulse sequences may also be 90° pulses, or may be at another angle appropriate to the selected imaging method used. In preferred embodiments, the proton magnetization exchange signal may be maximized by adjusting pulse angles of the first and second pulses. These pulse angles may indeed be adjusted to any degree of rotation which, when combined with the applied flip angle of the excitation pulse of the combined imaging sequence (the third pulse of the sequence used in magnetization exchange imaging) maximizes the proton magnetization exchange signal in the imaged result. For example, in a gradient echo imaging method, the flip angle of the excitation pulse is typically variable, and may be set anywhere between about 10° and about 90°. The first and second pulses in magnetization exchange imaging (MEXI) should thus preferably be adjusted to a combination of rotation angles which maximizes the intensity of the signal resulting from proton magnetization exchange between water molecule protons and macromolecule protons. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Tissue Temperature and Coagulation

Figure 3:
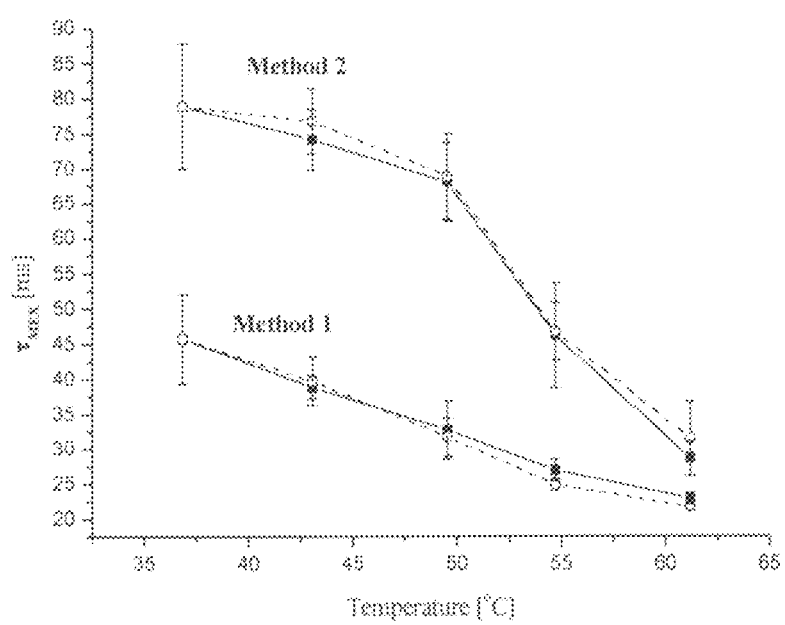
FIG. 3 presents experimental results demonstrating the independence of magnetization exchange time on temperature, and strong dependence of magnetization exchange time on coagulation of tissues.

Attention is now drawn to FIG. 3, which presents experimental results demonstrating the independence of $\tau_{MEX}$ on temperature and its strong dependence upon coagulation of tissues. Absolute values of $\tau_{MEX}$, acquired with methods described above, were measured at two stages: Data measured "during heating", shown as (-■-) was measured at the specified temperatures, after the tissue reached an equilibrium state of coagulation. Data obtained "post heating", and shown in the Figure as (---○---) was measured after tissue was heated to the specified temperature and then cooled to 37° C. Values are averages of 6 samples for each temperature except for 37° C. where the average is of 24 samples.

Results obtained "during heating" indicate the sensitivity of the NMR parameters both to temperature and coagulation. Results "post heating" indicate the effect of coagulation only. Coagulation of the tissue is the same both "during heating" and "post heating". The effect of temperature can be deduced from the difference between the "during" and "post" stages, as the only difference between those measurements is the temperature.

Using both of the calculation embodiments disclosed above, $\tau_{MEX}$ shows a profound decrease upon increase of the temperature of the thermal treatment, both during the heating procedure and after the sample temperature returned to 37° C. Using method A (described hereinabove) for creating the difference signal, $\tau_{MEX}$ decreases by a factor of 2.1 after the sample is heated to 62° C., relative to $\tau_{MEX}$ measured at 37° C. Using method B (described hereinabove) for creating the difference signal, $\tau_{MEX}$ decreases by a factor of 2.5 after the sample is heated to 62° C., relative to $\tau_{MEX}$ measured at 37° C. As seen from FIG. 3, the values of $\tau_{MEX}$ "post heating" are very similar to the values "during heating", despite the fact that their actual measurements were performed at different temperatures. These data demonstrate that temperature has little effect on measurements of $\tau_{MEX}$ in relevant temperature ranges.

Example 2

Imaging of Porcine Liver Tissue

Attention is now drawn to FIG. 4, which presents the results of an imaging experiment demonstrating the principles disclosed herein. For this imaging experiment a tube containing two layers of porcine liver separated with a thin Teflon disk was prepared. A first layer was of non-treated porcine liver. A second layer was of porcine liver after thermal treatment which included immersing a tube containing the liver in water at 65° C. for 15 minutes. After heating of the second layer, the whole sample (both layers) was immersed in fluorinated oil (Fluorinert, FC-77, from 3M Inc.). The fluorinated oil is of low water solubility, and its magnetic susceptibility is similar to that of water. It was used to improve magnetic field homogeneity.

Figure 4A:
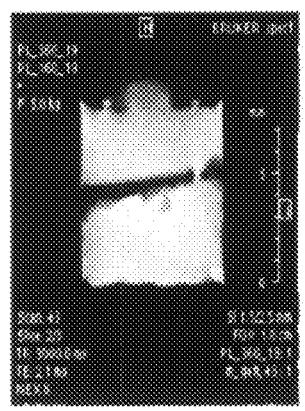
FIG. 4 presents results of an imaging experiment demonstrating the capability of a display based on measure of magnetization exchange time to distinguish between coagulated and non-coagulated tissue.

The sample was imaged using MEXI imaging as disclosed hereinabove, and to provide a basis for comparison the sample was also imaged with fast gradient echo imaging (GEFI). FIG. 4a shows the sample images as acquired with GEFI. As may be seen from the image, the entire sample may be seen.

Figure 4B:
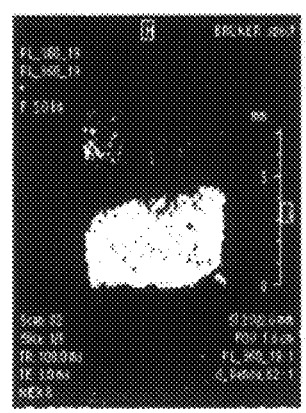
Figure 4C:
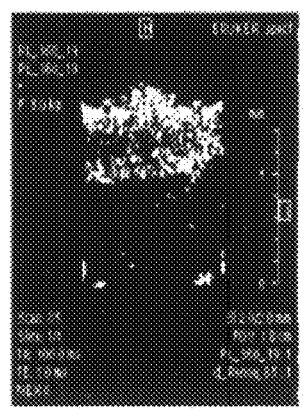

FIGS. 4b and 4c present MEXI images, at identical gray scale levels. In FIG. 4b, a signal generated using a $t_{zq}$ of 40 ms was subtracted from a signal generated using a $t_{zq}$ 10 μs, according to the first embodiment method disclosed above. In FIG. 4c, a signal based on a $t_{zq}$ of 100 ms was subtracted from a signal based on a $t_{zq}$ of 10 μs. For both images, a r of 400 μs was used.

In the three images presented in FIG. 4, the lower layers of porcine liver is of thermally treated liver, treated as described above. The upper layer in each image is of non-treated porcine liver. FIG. 4a presents fast gradient echo imaging (GEFI), with TE=2.14 ms, TR=3 sec, matrix size is 128×128, 8 repetitions, FOV 18×18 mm, and slice thickness 1.5 mm. FIGS. 4b and 4c present magnetization exchange imaging (MEXI) with fast spin echo (4 echoes in a single train). In these images TE=3.04 ms, TR=500 ms, matrix size=128× 128, FOV: 18×18 mm, and 8 repetitions, and slice thickness of 2 mm. In FIG. 4b, where a signal with $t_{zq}$ of 40 ms was subtracted from a signal with $t_{zq}$ of 10 μs, the porcine liver layer treated for 15 minutes in water at 65° C. may be observed. In FIG. 4c, where a signal based on $t_{zq}$ of 100 ms was subtracted from a signal based on $t_{zq}$ of 10 μs, the non-treated fresh liver may be seen. FIGS. 4b and 4c are presented with identical gray-scale levels.

Thus, FIG. 4 demonstrates that the contrast created by MEXI imaging can be used to distinguish between coagulated and non-coagulated tissue. At a $t_{zq}$ time of 40 ms, only the coagulated liver is observed. At a $t_{zq}$ time of 100 ms, only the non-coagulated liver is observed. Thus, MEXI imaging provides a new tool useable for monitoring thermal treatments.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of imaging a living tissue, comprising:
    (a) exposing said living tissue to a first set of MR pulses which result in a proton magnetization exchange between water molecules and macromolecules of said tissue, followed by
    (b) applying a first imaging sequence;
    (c) detecting spatially differentiated intensities of signals generated by applying said first imaging sequence following said proton magnetization exchange;
    (d) expressing said signal intensities as spatially differentiated contrast data of an image;
    (e) exposing said tissue to a second set of MR pulses, which second set does not result in a proton magnetization exchange between water molecules and macromolecules of said tissue, followed by applying a second imaging sequence;
    (f) calculating an image representing differences between signals detected from said first and from said second imaging sequences; and
    (g) calculating a difference between a first signal generated in response to a first pulse sequence of said MR pulses and a second signal generated in response to a second pulse sequence of said MR pulses, said first and second pulse sequences each having a first pulse, a second pulse, and a third pulse, wherein
        (i) a first time interval between said first and said second pulses of said first signal is sufficiently long to allow relaxation of transverse magnetization of said macromolecules and sufficiently short to prevent significant relaxation of transverse magnetization of said water molecules; and
        (ii) a second time interval between said second pulse and said third pulse of said first signal is sufficiently long to allow substantial transfer of magnetization from said water molecules to said macromolecules.

2. The method of claim 1, wherein a third time interval between said first and said second pulses of said second pulse sequence is sufficiently short to prevent substantial relaxation of transverse magnetization of said macromolecules during said third interval.

3. The method of claim 1, wherein a fourth time interval between said second pulse and said third pulse of said second pulse sequence is sufficiently short to prevent substantial transfer of magnetization from said water molecules to said macromolecules.

4. The method of claim 1, wherein said first pulses of said first and second pulse sequences are 90° pulses.

5. The method of claim 1, wherein said second pulses of said first and second pulse sequences are 90° pulses.

6. The method of claim 1, wherein said third pulses of said first and second pulse sequences are 90° pulses.

7. The method of claim 1, wherein said third pulse of at least said first pulse sequence is a selective pulse coordinated with use of a standard MRI imaging technique.

8. The method of claim 7, wherein said third pulse of at least said first pulse sequence is a selective pulse followed by a fast spin echo.

9. The method of claim 7, wherein said third pulse of at least said first pulse sequence is a selective pulse followed by a gradient echo.

10. The method of claim 2, further comprising selecting a timing delay for said second interval such that a signal is detected from coagulated tissue.

11. The method of claim 2, further comprising selecting a timing delay for said second interval such that no signal is detected from coagulated tissue.

12. The method of claim 3, further comprising selecting a timing delay for said second interval such that a signal is detected from coagulated tissue.

13. The method of claim 3, further comprising selecting a timing delay for said second interval such that no signal is detected from coagulated tissue.

14. The method of claim 1, wherein said first time interval between said first and said second pulses of said first pulse sequence is different from a third time interval between said first and said second pulses of said second pulse sequence.

15. The method of claim 1, wherein said second time interval between said second pulse and said third pulse of said first pulse sequence is different from a fourth time interval between said second pulse and said third pulse of said second pulse sequence.

16. The method of claim 1, wherein said third pulses of said first and second MR pulse sequences are soft pulses used for slice selection as part of an MR imaging technique.

17. The method of claim 1, wherein said MR pulses are soft pulses.

18. The method of claim 1, wherein said first pulses and second pulses of said first and second MR pulse sequences are soft pulses suitable for use in a clinical scanner.

19. The method of claim 1, further comprising imaging an effect of a treatment of said living tissue by treating said tissue and imaging a characteristic of said treated tissue.

20. The method of claim 19, wherein said treating of said tissue comprises thermal treatment of said tissue.

21. The method of claim 19, wherein said imaged characteristic is a coagulation state of said tissue.

22. The method of claim 19, further comprising imaging said tissue during treatment of said tissue to thereby monitor changes in a characteristic of said tissue during said treatment.

23. The method of claim 19, further comprising imaging said tissue subsequent to treatment of said tissues to thereby monitor changes in a characteristic of said tissue subsequent to said treatment.

24. The method of claim 19, wherein said tissue is liver tissue.

* * * * *